(12) United States Patent
Sarstedt et al.

(10) Patent No.: US 6,824,741 B2
(45) Date of Patent: Nov. 30, 2004

(54) APPARATUS AND METHOD FOR CARRYING OUT TESTS TO DETECT PARTICLES IN URINE

(75) Inventors: Walter Sarstedt, Nümbrecht (DE); Dagmar Flach, Gummersbach (DE); Horst Färber, Nümbrecht (DE); Petra Gross, Wiehl (DE)

(73) Assignee: Starstedt AG & Co., Numbrecht (DE)

( * ) Notice: Subject to any disclaimer, the term of this patent is extended or adjusted under 35 U.S.C. 154(b) by 0 days.

(21) Appl. No.: 10/244,034

(22) Filed: Sep. 13, 2002

(65) Prior Publication Data

US 2003/0064528 A1 Apr. 3, 2003

(30) Foreign Application Priority Data

Sep. 14, 2001 (DE) .......................................... 101 45 424

(51) Int. Cl.[7] .............................. B01L 3/00; G01N 1/00; G01N 21/03
(52) U.S. Cl. ........................... 422/102; 422/99; 422/58; 422/939; 436/164; 436/174; 600/573; 600/584
(58) Field of Search ............................ 422/99, 102, 55, 422/58, 939, 940; 435/288.1, 288.2; 600/573, 574, 580, 584; 436/174, 164

(56) References Cited

U.S. PATENT DOCUMENTS

| | | | | |
|---|---|---|---|---|
| 3,774,455 A | * | 11/1973 | Seidler et al. ................. | 73/444 |
| 3,859,671 A | * | 1/1975 | Tomasello ................... | 4/144.1 |
| 3,894,845 A | * | 7/1975 | McDonald ................... | 422/61 |
| 4,335,730 A | * | 6/1982 | Griffin ......................... | 600/573 |
| 4,473,530 A | * | 9/1984 | Villa-Real .................... | 422/58 |
| 4,741,346 A | * | 5/1988 | Wong et al. ................. | 600/573 |
| 5,498,395 A | * | 3/1996 | Moore et al. ............... | 422/100 |
| 5,897,840 A | * | 4/1999 | Owens et al. ............... | 422/102 |
| 6,027,939 A | * | 2/2000 | Grases Freixedas et al. .. | 436/74 |
| 6,401,552 B1 | * | 6/2002 | Elkins ......................... | 73/863 |
| 2003/0021727 A1 | * | 1/2003 | Weyker et al. ............... | 422/58 |

FOREIGN PATENT DOCUMENTS

| | | | |
|---|---|---|---|
| GB | 2131298 | * | 6/1984 |
| JP | 11-64183 | * | 3/1999 |

* cited by examiner

*Primary Examiner*—Maureen M. Wallenhorst
(74) *Attorney, Agent, or Firm*—Herbert Dubno

(57) ABSTRACT

A device for carrying out a test for the detection of particles in urine, especially for carrying out a test to determine the susceptibility of a test subject for kidney stones, whereby urine from the test subject is taken and collected and then the detection test is carried out, whereby the urine after a stand time is poured out of the test vessel, whereby the residue of test particles may be present in the test vessel is detected subsequently by the addition of a detection reagent, especially a dye reagent for optical detection, especially for a self test by a test subject, for example, at home. The device having a collecting vessel in which the urine is directly collected from the test subject and which also simultaneously forms the test vessel. The test vessel is column shaped and tapered toward its bottom and upwardly transitions into an overflow region. A closure element penetrates into the overflow region and displaces possible excess urine into the overflow region of the test vessel to close the latter and establish a defined test urine quantity therein.

11 Claims, 1 Drawing Sheet

APPARATUS AND METHOD FOR CARRYING OUT TESTS TO DETECT PARTICLES IN URINE

FIELD OF THE INVENTION

The present invention relates to an apparatus and a method for carrying out a test to detect particles in urine, especially for carrying out a test to determine the susceptibility of a test subject to kidney stones whereby urine is taken from the test subjects and collected and the detection test is carried out whereby the urine after a stand time is poured out of the test vessel and residues of particles which may be present in the test vessel are subjected to an optical recognition, especially by treating them with a detection reagent, especially a dye reagent.

BACKGROUND OF THE INVENTION

Such a kidney stone test is known from EP 0 889 326 which also proposes a modular system for carrying out the kidney stone test. In order to test the urine characteristics of a patient with respect to the susceptibility to kidney stones, the urine is checked as to whether calcium rich salts or particles precipitate. It is known to carry out the following significant steps in succession:

pouring 40 ml of directly obtained urine from a test subject into a petri dish or into a dish disposed centrally of a petri dish which contains a reaction substrate;

allowing a stand time (6 to 24 hours) to precipitate calcium particles;

discharging the petri dish contents and then washing with distilled water;

adding 400 $\mu$l of a dilute aqueous HCl solution to the reaction substrate;

adding 150 $\mu$l of an aqueous sodium acetate solution (5%, w/v) and adding 150 $\mu$l of the indicator solution Arsenazo III (0.1%, w/v and mixing for 15 seconds;

then optically obtaining the test results in the form of a pink coloration of the solution in the case of a nonsusceptible test subject or a blue coloration of the solution in the case of a susceptible test subject whereby the blue coloration can have a shading from violet to blue. At the boundary region between a positive and negative result, the solution has a pink coloration with a slight bluish tint.

It is important that the test be carried out with freshly obtained and thus still warm urine to avoid possible falsification of test results by premature precipitation because of cooling down.

The assembly for carrying out the test has a petri dish with a cover together with a smaller central dish for receiving the reaction substrate and the required reagent.

This method or system has the following drawbacks:

Since the urine must be added to the petri dish while warm, a separate collection container is required for transferring the urine. Since the test should also be capable of being used as a preliminary test by the test subject at home, the test subject optionally must be provided with a written advisory to the effect that the urine must be collected in a separate container and directly added to the petri dish while warm. In addition, the test subject or user must add a definite quantity of the urine, namely, exactly 40 ml to the petri dish which makes a prior measurement of the urine quantity necessary. While the petri dish has a cover in the known system, possible transport of the petri dish is exceptionally difficulty and impractical especially for older people.

The known method of detecting positive or negative kidney stone suspicions requires a number of operative steps like washing and supplying a number of reagents and the use of exact quantities of liquids which are added as well as the observation of time constraints for handling, like for example agitation. The reagent Arsenazo III is also toxic and creates disposal problems for the user.

The test results are determined by the color of the solution and precisely in the boundary region (pink coloration with weak bluish tint) between a clearly positive or negative result is difficult to recognize which is affected by the fact that the positive result is a blue coloration ranging from the violet to the blue.

OBJECTS OF THE INVENTION

It is the object of the invention to provide an improved apparatus for carrying out a test for detecting particles in urine.

It is also an object of the invention to provide an improved method for carrying out such a test whereby these drawbacks are avoided.

Another object of the invention is to eliminate drawbacks of prior art methods of detecting susceptibility of a human patient or subject to kidney stones.

SUMMARY OF THE INVENTION

From an apparatus point of view, the object is achieved in that the apparatus has a collecting vessel in which the urine of the test subject can be directly collected and which simultaneously is also the test vessel. Thus the test vessel is column shaped or tubular, tapers toward the bottom and extends upwardly into an overflow region, preferably formed in one piece on the test vessel which preferably has a setpoint level mark for the required filling state for the orientation of the test subject. In addition, the apparatus has a closure element which plugs into the collecting vessel or the overflow region and expels any excess urine which may have collected into the overflow region in order to establish a defined quantity of the test urine in the test vessel and close the latter. Preferably the device has means forming a stand for the automatic positioning of the collecting vessel with a vertical orientation during the stand time.

From the method view point, the object is achieved in that the following steps are carried out for a urine test according to the invention:

collecting the urine from the test subject directly in a collecting vessel which serves simultaneously also as the test vessel where the test vessel is preferably column shaped and tapered toward the bottom and has an overflow region into which the column transitions upwardly whereby the test subject can optionally be oriented by a marking on the overflow region showing the full state or by collecting the urine in a collecting vessel whose contents are transferred into a test vessel;

preferably allowing excess above the volume of the test vessel of the collected urine to run off into the overflow region;

closing the collecting container preferably with a closure element and expressing the excess urine which may be present in the overflow region to establish a defined quantity of test urine in the test vessel or closing the test vessel, waiting a predetermined stand time;

pouring off urine from the collecting container or the test vessel;

adding a detection reagent to the test vessel, especially in the convergingly shaped lower part of the test vessel. When required a strong acid, like HCl, can be added before the dye reagent is added.

The proposed apparatus for carrying out the test and the method has the following advantages and enables the following preferred further developments:

the test subject or the patient can collect the urine directly in the test vessel. It thus is insured that the urine, as is absolutely necessary for the test, is collected warm in the vessel and is not cooled by otherwise required handling as, for example, transfer.

The amount of urine required for the test is insured by the fact that the test subject can be oriented on the one hand by the level marking and on the other hand by the overflow region and the closure element which has a liquid displacement effect guaranteeing the correct test quantity so that after an ordinary closure within the test vessel, the required amount of urine is present. That means that the closure element, which preferably can be a screw closure, engages in the preferably funnel shaped overflow region and seals the test vessel with a defined volume at the end of the screw tightening process.

The test vessel—as the lower part of the collecting vessel—is column shaped or tube shaped according to the invention and has its bottom convergingly shaped or tapered and thus has a plug shape. This insures that the particles precipitating from the saturated urine solution will be concentrated at a limited location upon settling.

As the detection reagent, a dye reagent is selected which is neither toxic nor poisonous, for example, from the group of calcium indicators.

Such dye reagents have the advantage that they enable a clearer indication of the test results than the dye reagent of EP 0 889 326, in that the colors are clearly differentiable. Thus negative results are indicated by a strawberry red color or gray while positive results are indicated by a dark red or green.

To facilitate the reading of the results by the user with the aid of different dyes, the tapered bottom of the column shaped test vessel can additionally have a cuvette-like extension in which the dye reagent can preferably be added. The aforedescribed geometry enables good optical discrimination of different color results.

BRIEF DESCRIPTION OF THE DRAWING

The above and other objects, features, and advantages will become more readily apparent from the following description, reference being made to the accompanying drawing in which.

SPECIFIC DESCRIPTION

Figure 3:
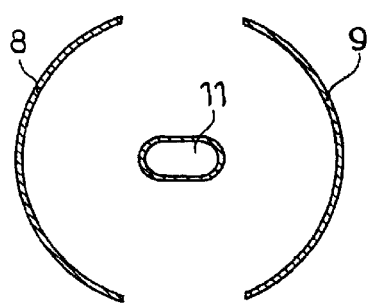
FIG. 3 is a cross section along line III—III of FIG. 1.

The overall apparatus 1 for carrying out a kidney stone test has a collecting container 2 which simultaneously is also the test vessel 3, a screw closure as the closure element 4 as well as a stand means 5 for the collecting vessel 2 altogether and which can be formed in one piece with a wall 6 of an overflow region 7 developed downwardly so that two half shells 8 and 9 form reliable stand surfaces (compare FIG. 3).

The collecting container 2 itself is comprised of the lower test vessel 3 and the overflow region 7 extending upwardly in one piece therewith and of a funnel shape. The collecting vessel 1 2 can be injection molded with the stand means 5 or the surfaces 8,9 in one piece from plastic.

The test vessel 3 is of an elongated plug shaped configuration which downwardly converges conically, whereby the taper 10 runs into a cuvette-like projection 11 which, because of its geometry, supports the concentration of the sedimenting particles and enables a better optical differentiation of the different colors produced by the dye reagent. In addition, the mixing of the dye reagent and possibly present particles to be detected is facilitated.

The test vessel 3, depending upon the test type, has a urine quantity of the corresponding volume, here for example, 24 ml.

At its top the test vessel 3 is connected to the funnel shaped overflow region 7 whose diameter $d_u$ is continuously greater than the diameter $d_r$ of the test vessel at its upper end. On this overflow region 7 an externally visible level mark 12 is applied which the test subject can be utilized for orientation upon collecting the urine. To close the collecting container 2, a closure element 7 is used. The element 7 is assembled from a displacement body 13 extending over the height $H_u$ of the overflow region 7 and having lateral projections 14 and a somewhat recessed contact surface 15. The closure element 7 also has a screw thread 17 radially spaced from the displacement body by means of a clamping element 16 bridging to the overflow region 7, and which can be screwed into the collecting container 2 filled with urine. A portion of the urine which exceeds the desired test quantity $V_{soll}$ in the test vessel is displaced by the immersion of the displacement body 13 upon the screwing of the cover in and the latter adjusts the exact urine quantity $V_{soll}$ without requiring the test subject to undertake any measurement.

Because of the displacement effect, the urine column 18 rises in the overflow region 7 from a first level I at about the height of the level marking 12 to a level II for the closed container. The level marking 12 has two important advantages, firstly it insures that sufficient urine will be collected in the collecting container to permit the requisite test quantity to be assured in every case and secondly it insures that the displaced urine quantity will not be so great that urine upon rising in the urine column will emerge from the overflow region. In this manner, the test device proposed can be simply manipulated even if self testing at home.

Figure 1:
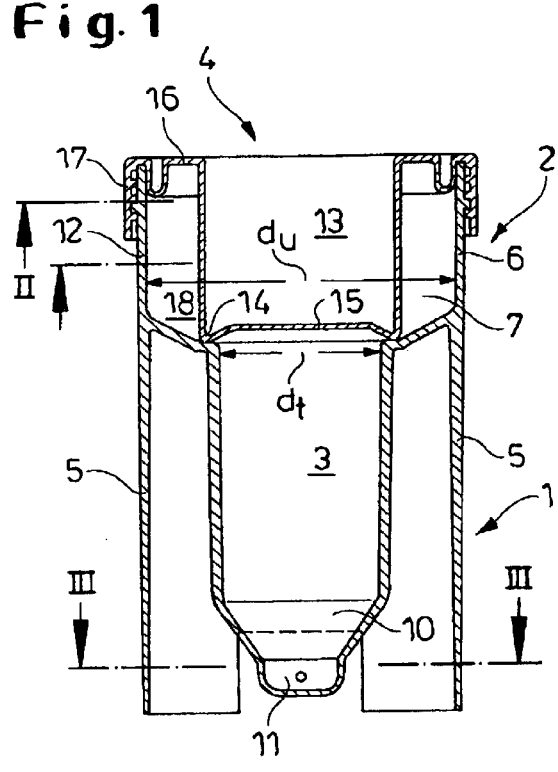
FIG. 1 is a sectional elevation of the apparatus according to the invention for carrying out a kidney stone test.
Figure 2:
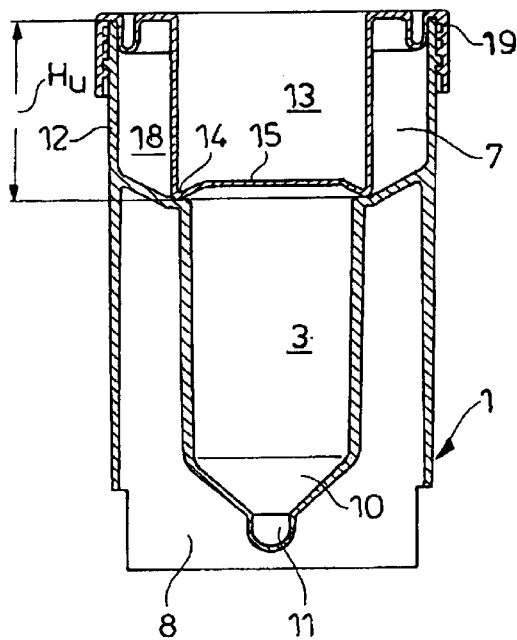
FIG. 2 is a sectional elevation of the apparatus of FIG. 1, rotated through 90°.

The juxtaposition of the two sections of FIGS. 1 and 2, whereby the same parts have corresponding reference characters, clearly shows the geometry of the cuvette-like projection, which has somewhat a channel shape.

The form of the stand 5 is detailed in FIG. 3. The stand surfaces or feet are formed by two half shells 8, 9 which are formed out of the overflow region wall in the upper part of the container. The upper region wall has an external thread 19 to allow the screw closure to be threaded on from above. These stand feet insure that the collecting container 2 can be securely held erect for the duration of the standtime in a vertical orientation of the test vessel 3 whereby the spacing of the half shells 8,9 forms a viewing window for the test vessel 3 and especially its bottom region 10 with the cuvette-shaped projection 11.

Figure 4:
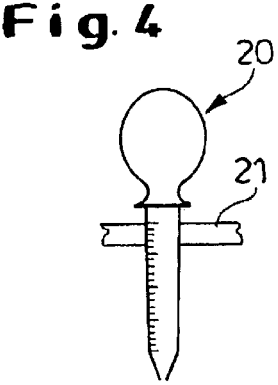
FIG. 4 is an elevational view of a pipette for the dye reagent which can be attached to the apparatus 1, e.g. by a clip, a part of which has been shown broken away in FIG. 4 for a modular apparatus.

The kidney stone test can be used as part of a modular system since the device in the form of a collecting container with an integrated test vessel as well as, for example, a single use pipette filled with the dye reagent, whereby the volume of the dye reagent should be approximately in the millimeter range. The pipette 20 of FIG. 4 may be attached to the vessel 1 by the clip when the single use pipette is prefilled with the dye reagent and is packaged with the vessel 1 for home use by the test subject or patient.

The proposed apparatus and method are not limited to a kidney stone test but can find use also for other urine tests. The kidney stone test is especially useful as a self test for home use but also as a preliminary test in apothecary or medical practice or optionally in hospitals.

We claim:

1. An apparatus for carrying out a test for the detection of particles in urine to determine the susceptibility of a test subject for kidney stones comprising a test vessel and whereby urine is obtained from the test subject and collected in the test vessel and then the detection test is carried out, whereby the urine after a stand time is poured out of the test vessel and possible particles are retained in the test vessel following which test results are obtained by the use of a detection reagent in the form of a dye reagent for optical detection, the apparatus further comprising:

a collecting container in which the urine is directly collected from the test subject and which serves simultaneously as the test vessel, the test vessel being column shaped at a lower portion and tapered downwardly toward a bottom and having an upwardly widening transition into an overflow region above said lower portion; and a closure element, which projects into the overflow region, displaces any excess urine upwardly into the overflow region of the test vessel, closes the lower portion of the test vessel and establishes a defined quantity of the test urine therein while also separating the lower portion from the overflow region, said closure element also closing said overflow region.

2. A method of carrying out a test for the detection of particles in urine to determine the susceptibility of a test subject for kidney stones whereby urine is obtained from the test subject and collected in a test vessel and then the detection test is carried out, whereby the urine after a stand time is poured out of the test vessel with a residue remaining of any particles which may be present in the test vessel with subsequent determination of a test result with a detection reagent in the form of a dye for optical detection, comprising the steps of:

collecting urine from the test subject directly in a collecting vessel which is simultaneously also the test vessel, closing the test vessel with a urine-displacing closure to displace urine upwardly into an overflow region located above said test vessel, waiting a predetermined stand time, pouring out the urine from the test vessel, and adding said detection reagent to the test vessel in a downwardly convergingly formed lower part of the test vessel.

3. Apparatus for testing urine to determine susceptibility of a test subject to kidney stones, comprising:

a one-piece test vessel having:
      an upright tubular cylindrical portion,
      a conically converging lower portion tapering downwardly from said cylindrical portion,
      a narrow cuvette-shaped bottom portion below said lower portion for collecting particles precipitated from urine in said vessel,
      an upwardly diverging portion at an upper end of said tubular cylindrical portion, and
      a cylindrical upper portion above and adjacent said upwardly diverging portion for collecting urine directly from a test subject, said upper portion being of greater diameter than said cylindrical portion; and
   a closure projecting into said upper portion and affixed to said upper portion for displacing excess urine in said tubular cylindrical portion upwardly whereby a fixed volume of urine is provided within said cylindrical portion and said closure seals said cylindrical portion with said fixed volume of urine therein so as to separate the cylindrical portion from the upper portion, while displacing excess urine upwardly into an overflow region wherein said overflow region is formed in the upper portion of the test vessel.

4. The apparatus defined in claim 3 wherein said closure has an internal screw thread engaging an external thread on an outer wall of said upper portion.

5. The apparatus defined in claim 4 wherein said closure has a portion projecting into engagement with said upwardly diverging portion around a mouth of said cylindrical portion to seal said cylindrical portion with said fixed amount of urine therein.

6. The apparatus defined in claim 5 wherein said closure is provided with a clamping element engaging an inner surface of said wall.

7. The apparatus defined in claim 6 wherein said vessel is formed with an externally visible level mark for indicating to the test subject a quantity of urine to be collected in said vessel.

8. The apparatus defined in claim 7, further comprising a stand formed in one piece with said vessel and enabling said cylindrical portion to be maintained in a vertical orientation for a stand time of urine in said vessel.

9. The apparatus defined in claim 8, wherein said stand comprises a pair of half shells extending downwardly from said wall with a spacing between them, contents of said bottom portion being visible between said half shells.

10. The apparatus defined in claim 9 wherein said vessel is molded in one piece from a transparent synthetic resin.

11. The apparatus defined in claim 10, further comprising a single use pipette containing a dye reagent for introduction into said vessel for optical detection of particles precipitated from the urine, said pipette having an outlet positionable to discharge into said vessel.

* * * * *